(12) United States Patent
Brannan

(10) Patent No.: US 9,743,975 B2
(45) Date of Patent: Aug. 29, 2017

(54) THERMAL ABLATION PROBE FOR A MEDICAL DEVICE

(71) Applicant: COVIDIEN LP, Mansfield, MA (US)

(72) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 84 days.

(21) Appl. No.: 14/016,870

(22) Filed: Sep. 3, 2013

(65) Prior Publication Data

US 2014/0094788 A1 Apr. 3, 2014

Related U.S. Application Data

(60) Provisional application No. 61/708,912, filed on Oct. 2, 2012.

(51) Int. Cl.

| A61B 18/14 | (2006.01) |
|---|---|
| A61B 18/12 | (2006.01) |
| A61B 18/18 | (2006.01) |
| A61B 18/00 | (2006.01) |
| A61B 90/00 | (2016.01) |

(52) U.S. Cl.
CPC .......... *A61B 18/1233* (2013.01); *A61B 18/14* (2013.01); *A61B 18/1482* (2013.01); *A61B 18/18* (2013.01); *A61B 18/1815* (2013.01); *A61B 2018/0016* (2013.01); *A61B 2018/00577* (2013.01); *A61B 2018/00791* (2013.01);
(Continued)

(58) Field of Classification Search
CPC .............. A61B 18/082; A61B 18/1233; A61B 2018/00642; A61B 2018/00797

USPC .......................... 606/31, 38, 34, 41; 607/102
See application file for complete search history.

(56) References Cited

U.S. PATENT DOCUMENTS

| D223,367 S | 4/1972 | Kountz |
|---|---|---|
| 4,136,566 A | 1/1979 | Christensen |

(Continued)

FOREIGN PATENT DOCUMENTS

| CN | 1103807 | 6/1995 |
|---|---|---|
| CN | 101389283 A | 3/2009 |

(Continued)

OTHER PUBLICATIONS

U.S. Appl. No. 13/419,981, filed Mar. 14, 2012, Joseph D. Brannan.
(Continued)

*Primary Examiner* — Thomas Giuliani

(57) ABSTRACT

A thermal ablation probe having one or more sensors for sensing at least one tissue parameter, such as temperature, fluctuation in temperature change, and/or rate of temperature change. The thermal ablation probe includes an elongated shaft and a head portion at a distal end of the elongated shaft. The head portion includes a sensing system having sensors for sensing the tissue parameter. The head portion further includes one or more antennas configured to apply energy to tissue. The proximal end of the thermal ablation probe is configured for removable engagement with a thermal ablation system. The one or more sensors form at least one thermal ablation probe array or sensing platform. The array (s) can be in operative communication with a control system for controlling the operation of the thermal ablation system in accordance with the at least one tissue parameter.

12 Claims, 4 Drawing Sheets

(52) U.S. Cl.
CPC ............... *A61B 2018/00797* (2013.01); *A61B 2090/065* (2016.02)

(56) References Cited

U.S. PATENT DOCUMENTS

| | | | |
|---|---|---|---|
| D263,020 S | 2/1982 | Rau, III | |
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| D354,218 S | 1/1995 | Van de Peer | |
| 5,685,839 A | 11/1997 | Edwards et al. | |
| 6,053,912 A * | 4/2000 | Panescu et al. | 606/40 |
| D424,693 S | 5/2000 | Pruter | |
| D424,694 S | 5/2000 | Tetzlaff et al. | |
| D425,201 S | 5/2000 | Tetzlaff et al. | |
| 6,113,593 A | 9/2000 | Tu et al. | |
| 6,117,131 A | 9/2000 | Taylor | |
| 6,290,717 B1 | 9/2001 | Philips | |
| D449,886 S | 10/2001 | Tetzlaff et al. | |
| D457,958 S | 5/2002 | Dycus et al. | |
| D457,959 S | 5/2002 | Tetzlaff et al. | |
| 6,402,742 B1 | 6/2002 | Blewett et al. | |
| 6,425,894 B1 | 7/2002 | Brucker et al. | |
| 6,451,011 B2 | 9/2002 | Tu | |
| D487,039 S | 2/2004 | Webster et al. | |
| D496,997 S | 10/2004 | Dycus et al. | |
| D499,181 S | 11/2004 | Dycus et al. | |
| 6,974,454 B2 | 12/2005 | Hooven | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,182,761 B2 | 2/2007 | Garabedian et al. | |
| 7,186,222 B1 | 3/2007 | Callister et al. | |
| D541,418 S | 4/2007 | Schechter et al. | |
| D541,938 S | 5/2007 | Kerr et al | |
| 7,303,332 B2 | 12/2007 | Yu | |
| D564,662 S | 3/2008 | Moses et al. | |
| 7,393,353 B2 | 7/2008 | Hooven | |
| D576,932 S | 9/2008 | Strehler | |
| D594,736 S | 6/2009 | Esjunin | |
| D594,737 S | 6/2009 | Kelly et al. | |
| 7,597,668 B2 | 10/2009 | Yarden | |
| D606,203 S | 12/2009 | Husheer et al. | |
| D613,412 S | 4/2010 | DeCarlo | |
| D634,010 S | 3/2011 | DeCarlo | |
| D681,810 S | 5/2013 | DeCarlo | |
| 2002/0019627 A1 | 2/2002 | Maguire et al. | |
| 2002/0120260 A1* | 8/2002 | Morris | A61B 18/1477 606/41 |
| 2003/0060819 A1 | 3/2003 | McGovern | |
| 2007/0287999 A1* | 12/2007 | Malecki | A61B 18/1492 606/41 |
| 2008/0161797 A1 | 7/2008 | Wang et al. | |
| 2008/0183251 A1* | 7/2008 | Azar et al. | 607/101 |
| 2009/0082837 A1 | 3/2009 | Gellman et al. | |
| 2009/0171344 A1* | 7/2009 | Pontis | A61B 18/1233 606/35 |
| 2009/0222002 A1 | 9/2009 | Bonn et al. | |
| 2009/0306638 A1 | 12/2009 | Hillely et al. | |
| 2010/0168557 A1* | 7/2010 | Deno | A61B 5/0422 600/424 |
| 2010/0280505 A1 | 11/2010 | Mattiuzzi et al. | |
| 2010/0331838 A1* | 12/2010 | Ibrahim | A61B 17/28 606/52 |
| 2011/0152853 A1 | 6/2011 | Manley et al. | |
| 2011/0184406 A1* | 7/2011 | Selkee | 606/41 |
| 2012/0136346 A1 | 5/2012 | Condie et al. | |
| 2012/0157890 A1 | 6/2012 | Govari et al. | |
| 2012/0232550 A1 | 9/2012 | Azure | |
| 2012/0239019 A1 | 9/2012 | Asconeguy | |

FOREIGN PATENT DOCUMENTS

| | | |
|---|---|---|
| CN | 102245118 A | 11/2011 |
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |

(56) References Cited

FOREIGN PATENT DOCUMENTS

| JP | 2001029356 | 2/2001 |
|----|------------|--------|
| JP | 2001037775 | 2/2001 |
| JP | 2001128990 | 5/2001 |
| JP | 2001231870 | 8/2001 |
| JP | 2008142467 | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 | 11/1974 |
| SU | 727201 | 4/1980 |
| WO | WO00/36985 | 6/2000 |
| WO | WO2010/035831 | 4/2010 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.

(56) References Cited

OTHER PUBLICATIONS

Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-3 I, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Themioradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, no. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.

(56) References Cited

OTHER PUBLICATIONS

T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology, "Overcoming the Challenge" located at: <http://www.urologix.com-!medicaUtechnology.html>Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
International Search Report dated Dec. 3, 2013 in International Appln. No. PCT/US2013/060278.
Extended European Search Report from Appl. No. EP 13844446.8 dated May 3, 2016.
Chinese Office Action issued in CN Appl No. 201380035209.5 dated Oct. 8, 2016.
Chinese Office Action and English language translation issued in CN Appl No. 201380035209.5 dated Jun. 7, 2017.

\* cited by examiner

THERMAL ABLATION PROBE FOR A MEDICAL DEVICE

CROSS REFERENCE TO RELATED APPLICATION

The present application claims the benefit of and priority to U.S. Provisional Application Ser. No. 61/708,912, filed on Oct. 2, 2012, the entire contents of which are incorporated herein by reference.

BACKGROUND

1. Technical Field

The present disclosure relates generally to a thermal ablation probe for a medical device, such as an ablation probe used in tissue ablation procedures. More particularly, the present disclosure is directed to a thermal ablation probe configured for contacting the surface of tissue and determining at least one tissue parameter, such as tissue temperature.

2. Background of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

During certain procedures, a probe may be inserted directly into tissue, inserted through a lumen, e.g., a vein, needle or catheter, or placed into the body using surgical techniques. Multiple probes may be used to synergistically create a large ablation or to ablate separate sites simultaneously.

In certain procedures, such as the ablation of tumor cells, it is often desirable to know the temperature of the tissue being ablated (or about to be ablated) and/or the temperature of the surrounding tissue. By monitoring the tissue temperature, an operator of a surgical instrument can determine whether the tissue temperature exceeded a certain temperature during a medical procedure. The operator can then decide to terminate the procedure and/or initiate a cooling procedure to cool the tissue.

SUMMARY

The present disclosure provides a thermal ablation probe having one or more sensors for sensing at least one tissue parameter, such as temperature. The present disclosure also provides a thermal ablation system having a thermal ablation probe and a generator. The generator delivers energy to the thermal ablation probe for ablating tissue during a medical procedure.

In particular, according to one aspect of the present disclosure a thermal ablation probe is provided which includes an elongated shaft, and a head portion at a distal end of the elongated shaft. The head portion defines a tissue contacting surface. The head portion includes one or more sensors in proximity to the tissue contacting surface for sensing one or a plurality of tissue parameters. The head portion further includes one or more antennas configured to apply energy to tissue. The tissue parameters may include temperature, fluctuation in temperature, and rate of temperature change. The one or more sensors are part of a sensing system.

The proximal end of the thermal ablation probe is configured for removable engagement with a thermal ablation system in operative communication with an energy delivering source, e.g., a generator. The generator delivers RF energy and/or microwave energy to the thermal ablation probe.

The sensor(s) may include a plurality of sensors forming a plurality of thermal ablation probe arrays each having a set of sensors of the plurality of sensors. At least one thermal ablation probe array may be in operative communication with a control system for controlling operation of the thermal ablation probe in accordance with sensed tissue parameter(s).

The head portion further defines one or more openings in the tissue-contacting surface. The sensor(s) is positioned within the corresponding opening(s) and may be movably positioned therein.

The head portion may include one or more sensors for sensing contact of the tissue-contacting surface of the head portion with tissue. The sensor(s) for sensing contact of the tissue-contacting surface of the head portion with tissue may be movably positioned within the one or more openings defined by the head portion.

According to another aspect of the present disclosure, a thermal ablation system is provided which includes a generator and a thermal ablation probe in operative communication with the generator. The thermal ablation probe includes an elongated shaft, and a head portion at a distal end of the elongated shaft. The head portion defines a tissue contacting surface. The head portion includes one or more sensors in proximity to the tissue contacting surface for sensing one or more tissue parameters. The head portion further includes one or more antennas configured to apply energy to tissue. The tissue parameter(s) may be temperature, fluctuation in temperature, and rate of temperature change. The generator delivers RF energy and/or microwave energy to the thermal ablation probe.

The thermal ablation system may further include a control system for controlling operation of the thermal ablation probe in accordance with the sensed tissue parameter(s).

The head portion may further define one or more openings in the tissue-contacting surface. The sensor(s) may be positioned within the corresponding opening. The sensor(s) may be movably positioned within the opening(s). The head portion further includes one or more sensors for sensing contact of the tissue-contacting surface of the head portion with tissue. The sensor(s) for sensing contact of the tissue-contacting surface of the head portion with tissue may be movably positioned within the opening(s) defined by the head portion.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail.

Figure 1:
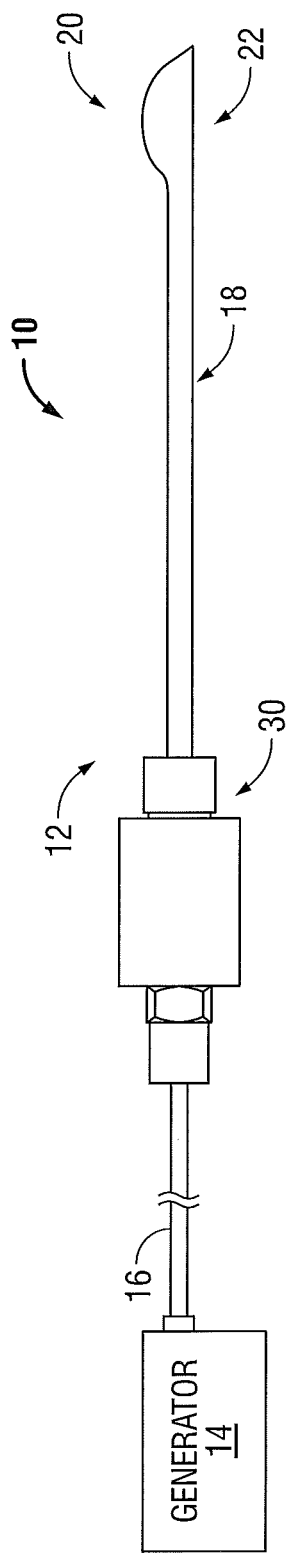
FIG. 1 is a schematic diagram of a thermal ablation system having a thermal ablation probe according to an embodiment of the present disclosure.
Figure 2:
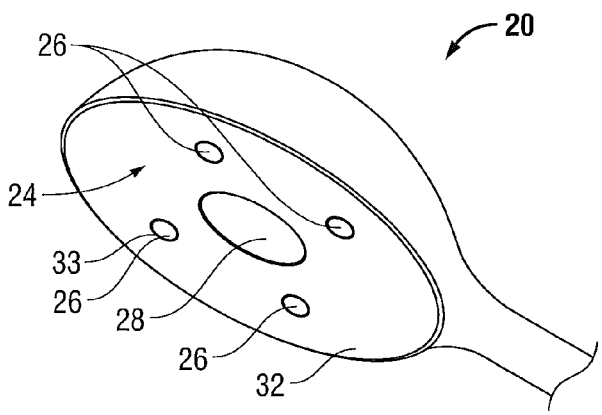
FIG. 2 is a perspective view of a head portion of the thermal ablation probe according to the present disclosure.
Figure 3:
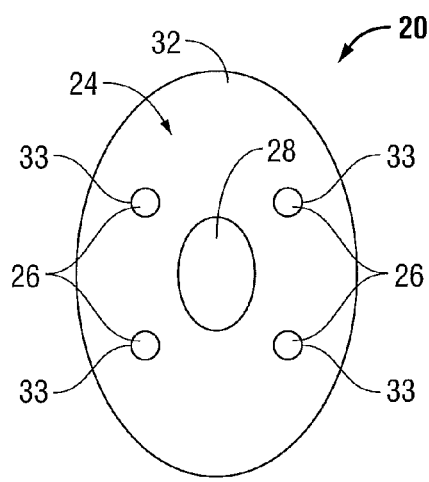
FIG. 3 is a front view of the head portion of the thermal ablation probe according to the present disclosure.

A thermal ablation system is described herein with reference to the various figures. With reference to FIG. 1, the thermal ablation system is designated generally by reference numeral 10. The thermal ablation system 10 includes a thermal ablation probe 12 coupled to a generator 14 via a cable 16. The thermal ablation probe 12 includes an elongated shaft 18 and a head portion 20 at a distal end 22 of the elongated shaft 18. The head portion 20 includes a sensing system 24 (FIG. 2) having one or more sensors 26 for sensing one or more tissue parameters, such as temperature, fluctuation in temperature, rate of temperature change, etc.

The head portion 20 further includes one or more electrodes and/or antennas 28 for applying energy to tissue for delivering energy to tissue, such as, for example, RF and/or microwave energy received from the generator 14. The antennas 28 can be configured in a monopolar or bipolar configuration. The antennas 28 can be configured with linear, aperture, waveguide, and/or microstrip topologies.

The proximal end 30 of the thermal ablation probe 12 is configured for removably securing the thermal ablation probe 12 to the thermal ablation system 10. Even though FIG. 1 illustrates the proximal end including a luer type connector, other types of connectors or securing mechanisms can be used.

With reference to FIGS. 2-5, there are shown perspective and front views of the head portion 20 of the thermal ablation probe 12. The head portion 20 of the thermal ablation probe 12 defines a tissue-contacting surface 32 having one or more openings 33 defined therein disposed in alignment with the one or more sensors 26 of the sensing system 24. The one or more sensors 26 are configured for sensing the one or more tissue parameters after the tissue-contacting surface 32 contacts tissue (see FIG. 6). The tissue-contacting surface of the sensors 26 is flush with the tissue-contacting surface 32 of the head portion 20.

Figure 5:
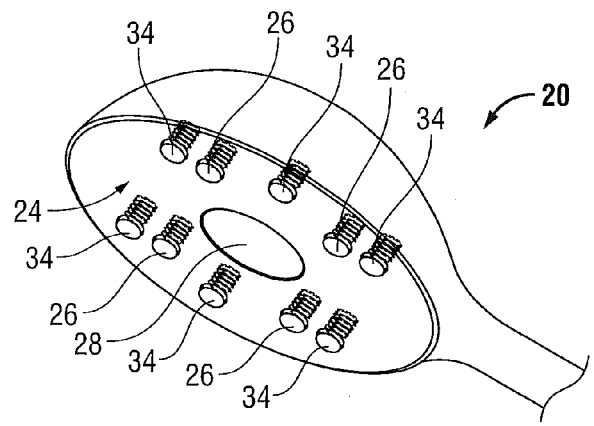
FIG. 5 is a front view of another alternate head portion of the thermal ablation probe having spring-biased sensors according to the present disclosure.
Figure 6:
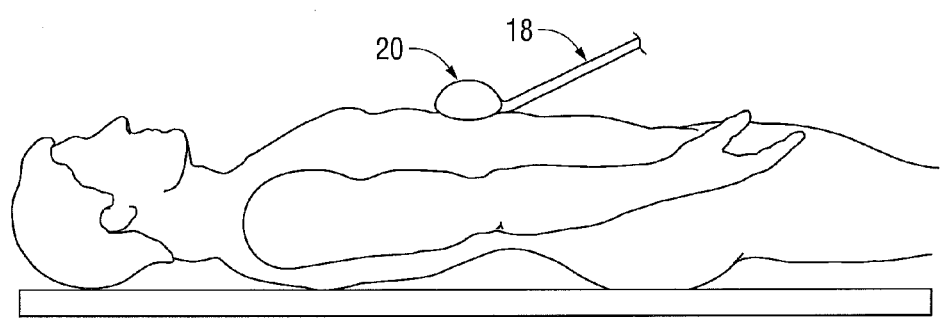
FIG. 6 is a perspective view of the head portion of the thermal ablation probe in full contact with tissue for sensing at least one tissue parameter, such as temperature, according to the present disclosure.

The sensors 26 may be configured to move or recede within the head portion 20 when the sensors 26 come into contact with tissue and are pressed against the tissue (see FIG. 5). The sensors 26 can be spring-biased as shown by FIG. 5 for moving or receding within the head portion 20 when a force is applied to an external surface of the sensors 26.

The sensors 26 may include one or more skin temperature monitoring devices, such as thermal ablation probes, thermocouples, thermistors, optical fibers and the like, to monitor tissue surface temperature, fluctuation in temperature, and/or rate of temperature change.

Figure 4:
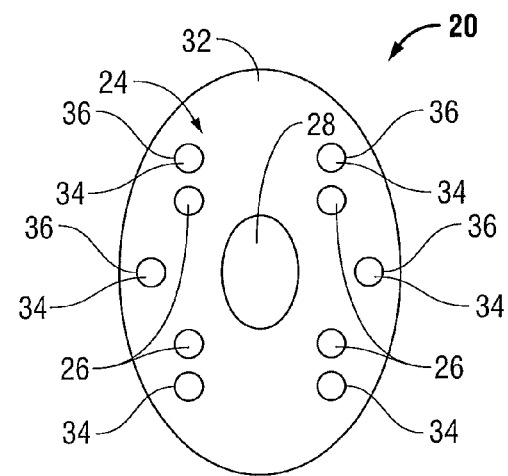
FIG. 4 is a front view of an alternate head portion of the thermal ablation probe according to the present disclosure.

In an alternate embodiment shown by FIG. 4, one or more tissue-contacting sensors 34 are provided in additional openings 36 defined in the head portion 20. The tissue-contacting sensors 34 are able to detect contact of the tissue-contacting surface 32 with tissue. The tissue-contacting surface of the sensors 34 is flush with the tissue-contacting surface 32 of the head portion 20.

The tissue-contacting sensors 34 may be configured to move or recede within the head portion 20 when the sensors 34 come into contact with tissue and are pressed against the tissue (see FIG. 5). The sensors 34 may be spring-biased as shown by FIG. 5 for moving or receding within the head portion 20 when a force is applied to an external surface of the sensors 34.

The tissue-contacting sensors 34 can detect contact of the tissue-contacting surface 32 of the head portion 20 by using one or more ultrasonic sensors, infrared sensors or other type of sensors capable of detecting contact of the head portion 20 with tissue.

Figure 7:
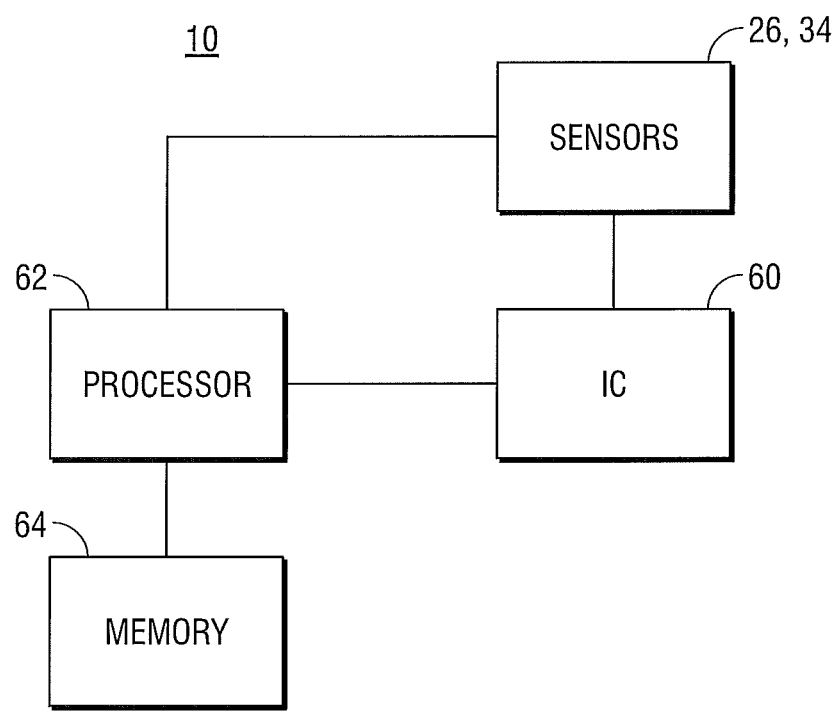
FIG. 7 is a schematic block diagram of the thermal ablation system according to the present disclosure.

With reference to FIG. 7, there is shown an exemplary block diagram of the thermal ablation system 10. Besides the components mentioned above, such as the sensors 26, 34, the thermal ablation system 10 includes additional circuit components, including, for example, an integrated circuit 60

(such as, for example, an ASIC) programmed to perform at least one function, such as performing a diagnostic test to ascertain the operability of the sensors 26, 34, a processor or controller 62, and a memory 64, within the head portion 20 and/or the elongated shaft 18. The circuit components receive and process signals from the sensors 26 and, in the alternate embodiment, from the sensors 26 and the tissue-contacting sensors 34.

By processing the signals received from the sensors 26, 34, the processor or controller 62 determine a value corresponding to the one or more tissue parameters, such as tissue temperature, and, in the alternate embodiment, determine if the tissue-contacting surface 32 is in full contact with tissue. A look-up table stored in the memory 64 may be used to correlate the value with the tissue parameter. The look-up table may be stored within the processor 62 or externally within a computing device, such as a personal computer.

The tissue-contacting surface 32 is determined to be in full contact with tissue (as shown by FIG. 5) if the signals received from each of the tissue-contacting sensors 34 indicate that each sensor 34 is in contact with tissue. The received signals can be analyzed by the processor 62 to determine if the signals are indicative of the sensors in full contact with tissue. At least one characteristic of the signal may be analyzed for making this determination, e.g., amplitude or frequency.

The processor or controller 62 may be programmed to prevent or stop operation of the thermal ablation system 10 and/or thermal ablation probe 12 if it is determined that the tissue-contacting surface 32 is not in full contact with tissue. Additionally, the processor 62 may also be programmed to prevent or stop operation of the thermal ablation system 10 and/or thermal ablation probe 12 if it is determined that the tissue parameter(s) is above or below a predetermined threshold stored in memory. For example, the processor 62 can be programmed to prevent operation or stop operation of the thermal ablation system 10 by disabling power to the thermal ablation probe 12, or to the antennas 28, when the tissue temperature is determined to be above, for example, 60 degrees Celsius.

Alternatively, the processor 62 can also be programmed to prevent operation or stop operation of the thermal ablation system 10 if there is a fluctuation in tissue temperature outside a predetermined range or the rate of temperature increase is outside a predetermined range.

The sensors 26, 34 of the sensing system 24 of the various embodiments described herein can form one or more thermal ablation probe arrays or sensing platforms. Each thermal ablation probe array or sensing platform may be independently controlled and/or monitored during a medical procedure. Each sensing platform may include only one type of sensor, or a combination of different types of sensors.

The thermal ablation probe arrays) may be in operative communication with a control system of the thermal ablation system 10 for controlling the operation of the thermal ablation system 10 and/or thermal ablation probe 12 in accordance with the sensed parameter(s). The control system may include, for example, one or more of the circuit components shown by FIG. 6, such as the processor 62. The sensing system 24 according to the present disclosure may be used to monitor in real-time the tissue temperature (or other tissue parameters) during energy delivery and use the information to deduce tissue state during a medical procedure, such as tissue ablation.

The generator 14 is configured to provide electromagnetic energy (e.g., high frequency electrosurgical energy and/or microwave energy at an operational frequency from about 100 kHz to about 10,000 MHz). The thermal ablation probe 12 is shown in the various figures as being able to deliver electrosurgical energy to tissue. The probe 12 can be of the type suitable for delivering microwave energy.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A thermal ablation probe comprising: an elongated shaft; and a head portion formed by a distal end of the elongated shaft and defining a planar tissue contacting surface configured to contact a tissue surface, the head portion comprising: a plurality of tissue contacting sensors configured to determine if the planar tissue contacting surface is in direct contact with the tissue surface; and at least one electrode configured to apply energy to tissue, the at least one electrode defining a planar surface coplanar with the planar tissue contacting surface and disposed at a center portion of the planar tissue contacting surface, wherein the at least one electrode is prevented from applying energy to tissue when it is determined that the planar tissue contacting surface is not in direct contact with the tissue surface, the plurality of tissue contacting sensors disposed on the planar tissue contacting surface and concentrically surrounding the at least one electrode, wherein the head portion further defines a plurality of openings in the planar tissue contacting surface, and wherein each of the plurality of tissue contacting sensors is movably positioned within a respective opening of the plurality of openings.

2. The thermal ablation probe according to claim 1, further comprising at least one temperature sensor configured to sense at least one tissue parameter selected from the group consisting of temperature, fluctuation in temperature, and rate of temperature change, wherein the at least one electrode is prevented from applying energy to tissue when the at least one tissue parameter sensed is outside a predetermined range.

3. The thermal ablation probe according to claim 1, wherein a proximal end of the elongated shaft includes a luer connector configured to releasably couple the thermal ablation probe with an energy delivering source.

4. The thermal ablation probe according to claim 3, wherein the energy delivering source is a generator.

5. The thermal ablation probe according to claim 4, wherein the generator delivers a type of energy to the thermal ablation probe selected from the group consisting of RF energy and microwave energy.

6. The thermal ablation probe according to claim 1, wherein the planar tissue contacting surface defines a plane disposed parallel to a longitudinal axis defined by the elongated shaft.

7. A thermal ablation system comprising: a generator; a thermal ablation probe in operative communication with the generator, said thermal ablation probe comprising: an elongated shaft; and a head portion formed by a distal end of the elongated shaft, wherein the head portion defines a planar tissue contacting surface configured to be positioned on an external tissue surface, the head portion comprising: a plurality of tissue contacting sensors configured to determine whether the planar tissue contacting surface is in direct contact with the external tissue surface; and at least one electrode configured to apply energy to tissue, the at least one electrode defining a planar surface coplanar with the planar tissue contacting surface and disposed at a center portion of the planar tissue contacting surface, wherein the at least one electrode is prevented from applying energy to tissue when it is determined that the planar tissue contacting surface is not in direct contact with the external tissue surface, the plurality of tissue contacting sensors disposed on the planar tissue contacting surface and concentrically surrounding the at least one electrode, wherein the head portion further defines a plurality of openings in the planar tissue contacting surface, and each tissue contacting sensor of the plurality of tissue contacting sensors is movably positioned within a respective opening of the plurality of openings.

8. The thermal ablation system according to claim 7, wherein the thermal ablation probe further comprises at least one temperature sensor configured to sense at least one tissue parameter selected from the group consisting of temperature, fluctuation in temperature, and rate of temperature change.

9. The thermal ablation system according to claim 8, wherein the at least one electrode is prevented from applying energy to tissue when the at least one tissue parameter sensed is outside a predetermined range.

10. The thermal ablation system according to claim 7, wherein the generator delivers a type of energy to the thermal ablation probe selected from the group consisting of RF energy and microwave energy.

11. The thermal ablation system according to claim 10, further comprising a control system for controlling operation of the thermal ablation probe in accordance with at least one sensed tissue parameter.

12. The thermal ablation system according to claim 7, wherein the planar tissue contacting surface defines a plane parallel to a longitudinal axis defined by the elongated shaft.

* * * * *